United States Patent [19]

McCall

[11] 4,319,584
[45] Mar. 16, 1982

[54] ELECTRICAL PULSE ACUPRESSURE SYSTEM

[76] Inventor: Francis J. McCall, 19231 Victory Blvd., Reseda, Calif. 91335

[21] Appl. No.: 151,184

[22] Filed: May 19, 1980

[51] Int. Cl.³ .............................................. A61N 1/36
[52] U.S. Cl. .................................... 128/789; 128/907
[58] Field of Search ........ 128/783, 784, 789, 791–793, 128/802, 907, 24.4, 24.5, 735, 303.13, 329 A, 419 R, 421, 422; 179/107 R, 107 H, 107 E

[56] References Cited

U.S. PATENT DOCUMENTS

| | | | |
|---|---|---|---|
| 1,623,552 | 4/1927 | Pollard ................................ | 128/789 |
| 3,025,858 | 3/1962 | Browner ............................. | 128/791 |
| 3,122,137 | 2/1964 | Erlanger ......................... | 128/793 X |
| 3,209,080 | 9/1965 | Guttner et al. ................. | 179/107 H |
| 3,598,928 | 8/1971 | Hickox ............................. | 179/107 E |
| 3,900,020 | 8/1975 | Lock ................................... | 128/735 |

FOREIGN PATENT DOCUMENTS 670303  6/1979  U.S.S.R. ............................. 128/791

*Primary Examiner*—Lee S. Cohen
*Attorney, Agent, or Firm*—Jack C. Munro

[57] ABSTRACT

An electrical pulse acupressure system which provides for an electrical pulse generator connected to an electrical pulse applicator. The entire unit may be located within the outer ear of a human being or the electrical pulse generator could be located exteriorly of the human ear. The electrical pulse applicator includes metallic nodules, each of which is to connect with a particular acupuncture point within the human body. The electrical pulse generator is capable of transmitting a plurality of different patterns of waveforms of electrical pulses. There is also provided an electrical pulse generator which is to be connected to a clip which is to be clasped onto a portion of the human body for the conducting of electrical pulses through acupuncture points.

6 Claims, 8 Drawing Figures

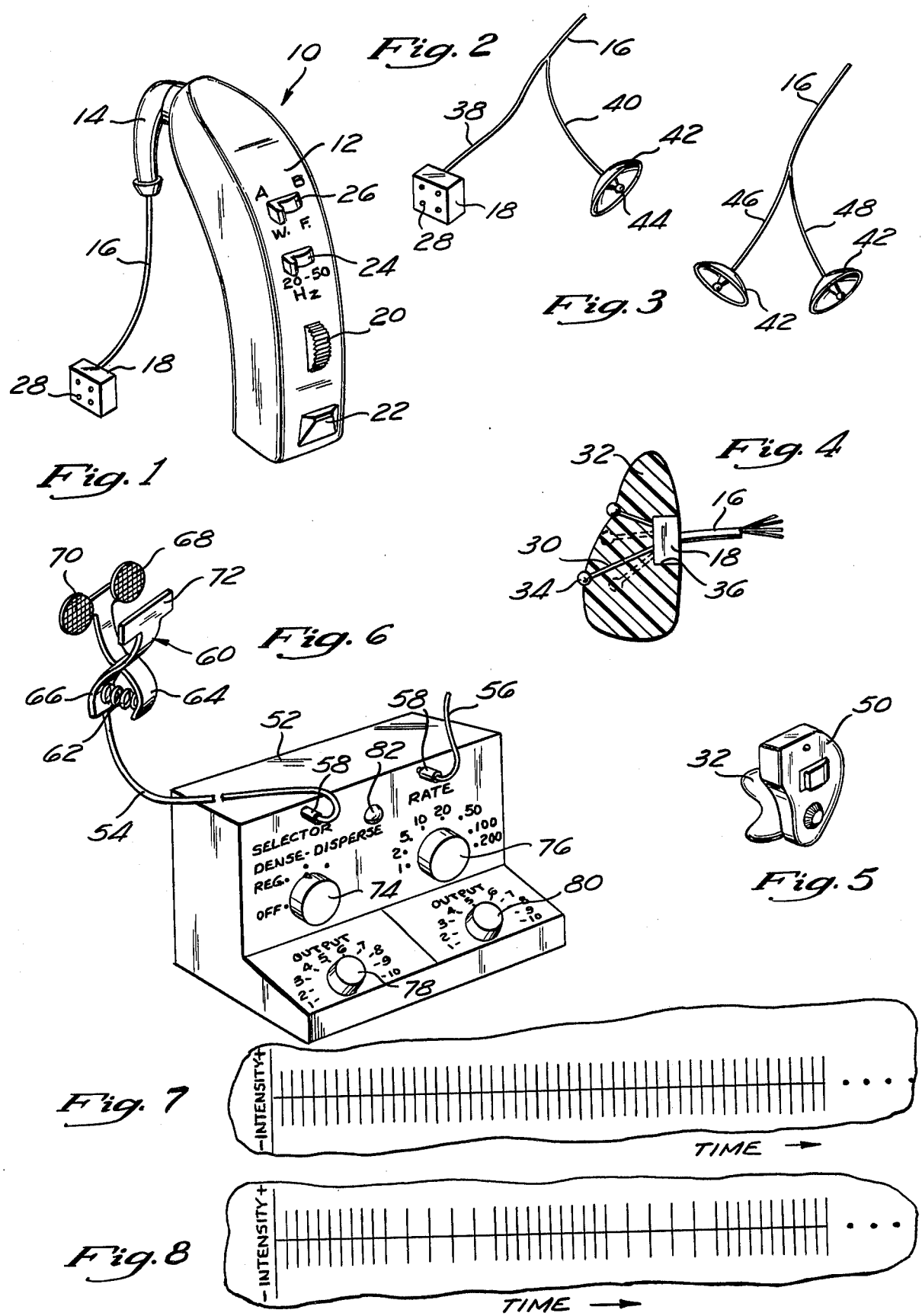

ELECTRICAL PULSE ACUPRESSURE SYSTEM

BACKGROUND OF THE INVENTION

The field of this invention relates to acupressure therapy and more particularly to improved acupressure systems in which small electrical pulses are continuously transmitted to selected acupressure points to achieve treatment.

The subject matter of this invention is to constitute an improvement over the structure defined within U.S. patent application Ser. No. 06/070,747 now U.S. Pat. No. 4,267,838, filed Aug. 29, 1979, entitled: APPARATUS FOR ELECTRICAL IMPULSE ACUPRESSURE TREATMENT, by the present inventor.

As was discussed in the aforementioned patent application, it is known that there are certain locations where acupuncture points on the ear and other parts of the body, which when subjected to acupuncture treatment, will have a therapeutic affect on corresponding body functions, reactions, muscles, organs, and the like. For example, one specific acupuncture point on the ear may influence throat reaction, another the mouth function, while still another, stomach activity. Location and stimulation of these sensitive acupuncture points with acupuncture therapy has been used to treat such conditions as obesity, alcoholism, drug addiction, smoking and the like.

Additionally, acupuncture points can be used to control pain. For example, it is known if a dentist were to employ the use of a properly applied acupressure device that pain, which would be sensed by the patient in the performing of drilling and other types of operations within the mouth, could be diminished by as great as seventy five percent. The diminishing of pain with the use of such a device has substantial advantages, with the primary advantage being that there is no drug used, and therefore, no after effect. Although the use of such a device is not recommended for all dental procedures, for dental procedures having a low threshhold of pain, the use of such a device for a substantial number of individuals would be satisfactory.

As was mentioned in the previous patent application, it has been known that it is not necessary to insert needles into the body in order to affect treatment of acupuncture points. Physical pressure applied against the specific point will achieve some degree of treatment and can be as effective as the insertion of a needle. The aforementioned patent application discloses a molded device which is to be located within the external ear and also a cup shaped applicator which is to be applied to other parts of the body.

The interior surface of each molded device includes one or more protruding members which are in the form of spherical nodules. Each nodule is to be located in a precise position against a certain acupuncture point. Thereby, treatment to the individual through the particular acupuncture point is achieved by pressure. Treatment is to be able to occur at the practioner's place of business and also the device can be worn by the user and therefore the patient can be treated when away from the practioner's place of business.

As previously mentioned in the aforementioned patent application, not only using pressure on the acupuncture point, but also the applying of pulses of electrical energy further enhances treatment. These pulses are at a very low current level and actually in most instances are not even felt by the patient. The use of these electrical pulses provide a more effective method of treatment in conjunction with the pressure applied to the acupuncture point.

SUMMARY OF THE INVENTION

The system of this invention relates to devices which employ both the physical pressure acupuncture device and also an electrical pulse treating of the acupuncture joint. A molded device is specifically attached to a body location over an acupuncture point. The inside surface of the molded device includes one or more protruding metallic nodules. An electrical conductor is electrically connected to each nodule. Electrical pulses are transmitted to each nodule in the form of a preselected wave pattern. The type of wave pattern can be varied and the current supplied to each nodule can be varied. Electrical power supply may be designed as a unit to be worn around the ear of the wearer or can be mounted on the exterior surface of the molded device itself and capable of being worn substantially within the external ear of the wearer. The molded device may also take the form of a clip having one or more waffle patterned pads. The clip is to be attached at a particular desired area of the patient's body. The power supply for such a clip is to be spaced from the patient and not worn thereby.

BRIEF DESCRIPTION OF THE DRAWING

FIG. 1 is a diagramatic perspective view of the first embodiment of the structure of this invention which is adapted to be located around the exterior of a human ear of the wearer;

FIG. 2 is a perspective view of a modified form of electrical connection which could be employed in conjunction with the structure of FIG. 1;

FIG. 3 is a view similar to FIG. 2, but of a further modified form of electrical connection which can be employed in conjunction with FIG. 1;

FIG. 4 is a cross-sectional view depicting a molded device which is to be employed in conjunction with the structure of FIG. 1, such molded device being previously defined and claimed within the aforementioned United States Letters Patent Application;

FIG. 5 is a diagramatic perspective view showing the electrical power supply being miniaturized and attached directly to a mold, such as to the exterior surface of the mold of FIG. 4, and the entire structure is adapted to be located within the external ear of the wearer;

FIG. 6 is a perspective view of a second embodiment of the structure of this invention in which a clip is employed which uses waffle pads and is adapted to be attached to a portion of the patients body and the power supply is to be located spaced from the patient's body;

FIG. 7 is a diagram depicting the regular type of waveform electrical pulse which is selectable by either of the devices of FIG. 1 or FIG. 6; and FIG. 8 is a view similar to FIG. 7 but of a different type of waveform representation.

DETAILED DESCRIPTION OF THE SHOWN EMBODIMENT

Referring particularly to the drawing, there is shown in FIG. 1 the first embodiment 10 of this invention, which takes the form of a housing 12, an extension 14, an electrical wire 16 and a plug 18. The wire 16 extends from within housing 12 within which is to be located a battery source (not shown) of electrical energy. The electrical energy source will be activated and deactivated by means of on/off switch 20. When the switch 20 is in the on position, an indicator light 22 will be lit. The frequency can be varied to be at either twenty Hertz or fifty Hertz, by selecting the corresponding position of switch 24. The twenty Hertz would be twenty pulses per second and fifty Hertz would be fifty pulses per second. The indicator light 22 visually displays the frequency. In other words, the indicator light flashes and will flash substantially slower at twenty Hertz than at fifty Hertz. The knob 20 is to also control intensity and with the knob 20 fully moved to the open position, the intensity (or power) would be at the fullest extent. If the knob 20 is turned only ten percent, then the intensity would be only ten percent of the maximum intensity.

Also mounted on the housing 12 is a movable knob 26. The knob 26 is to be movable either to a position denoted as A or to a position denoted as B. The knob 26 is used to select the type of waveform. In other words, if the knob is in position A, then the waveform shown within FIG. 7 will be selected, which is termed a regular type of waveform wherein the pulses of electrical energy are evenly spaced apart and are of the same intensity. If position B is selected, the waveform shown within FIG. 8 will be employed, that being what is termed dense and disperse. As is readily apparent from FIG. 8, the intensity is constant, but the pulses become farther apart in time and then proceed to come closer together in time, and so forth. In certain instances for certain types of treatment, it may be more desirable to use the waveform shown in FIG. 8 as opposed to the waveform in FIG. 7 and vice versa.

The actual electronics within the housing 12, in order to achieve the desired output pulses, is deemed to be conventional and forms no specific part of this invention.

The plug 18 includes a plurality of electrical connectors 28 (actually four in number). Each electrical connector 28 is to connect with an electrical conductor 30 formed within a molded plastic member 32. Each electrical conductor 30 terminates in a metallic nodule 34. The plug 18 is polygonal shaped and is adapted to fit in a close fitting manner within a recess 36 formed within the molded device 32. When the plug 18 is so located within the recess 36, each connector 28 connects with a respective electrical connector 30 which thereby supplies pulses of electrical current to the respective nodules 34. Each nodule 34 will receive a pulse of electrical energy at the same time and at the same intensity. For a more detailed description of the construction of the molded device 32 in conjunction with a plug 18, reference is to be had to the aforementioned patent application.

It is to be understood that the plug 32 will be adapted to be fitted within the interior of a human ear with each device 32 being manufactured specifically for each individual. It is also to be understood that each nodule 34 will connect with an acupuncture point within the person's ear.

The size of the housing 12 is selected so that it is readily locatable behind the individual's ear. The device 12 is held in position by means of the extension 14 which is conducted over the top of the ear and partially extends within the external ear. The wire 16 also lies within the external ear with the plug 18 cooperating with the device 32 which is located entirely within the external ear.

It is to be understood that the electrical wire 16 could be divided into separate electrical conductors 38 and 40.

The electrical conductor 38 could be connected to a plug 18, such as shown in FIG. 2 with the electrical conductor 40 being connected to an applicator disc 42. Such an arrangement is shown in FIG. 2 of the drawing. The disc 42 is basically cup shaped and has a metallic nodule 44 formed centrally and interiorly thereof. The disc 42 is to be coated interiorly with adhesive and applied directly to an acupuncture point on the patient's body other than within the ear. Nodule 44 is to press against the appropriate acupuncture point. For a more detailed explanation of the disc 42, reference is to be had again to the aforementioned patent application.

Referring particularly to FIG. 3 of the drawing, the electrical conductors 16 can also be divided into electrical conductors 46 and 48 each of which are connected to a disc 42.

Referring particularly to FIG. 5, the plug 32 may be directly connected to a housing 50 which supports electronic circuitry to provide the electrical pulse necessary to the nodules 34 of the device 32. The feature of the structure of FIG. 5 is that it is entirely worn within the external ear of the patient, where the structure of FIG. 1 is required to be primarily worn externally of the ear.

It is to be understood that the housing 50 will include appropriate knobs to select the waveform intensity and to vary the frequency in the manner similar to the housing 12.

The use of acupuncture points within the field of dentistry can be of significant value in decreasing pain without the use of drugs. In order to achieve this, a housing 52 is employed which is to be located on a separate supportive surface, such as a table. The housing 52 is to include appropriate electronic circuitry (not shown) which is capable of emitting electrical pulses into either wires 54 and/or 56. The wires 54 and 56 each include a removable engageable plug 58 which is to electrically engage with an opening on the left side of the housing 52 or an opening on the right side of the housing 52, as shown in FIG. 6. The electrical conductor 54 is to electrically connect with a clip 60 and electrical conductor 56 will also be connected to another similar clip (not shown). The purpose of the dual clips 60 is so that the dentist can locate one on one part of the patient's body, with the other clip to be located at another point of the patient's body. For instance, one clip 60 could be located on the right ear lobe, the other clip beng connected to the left ear lobe of the patient.

Each clip 60 is spring biased to the close position by means of a coil spring 62. Each clip 60 is to be opened by means of manually compressing the coil spring 62 between the handles 64 and 66. The outer end of the handle 66 is divided into a pair of pads 68 and 70. The outer end of the handle 66 comprises a plate 72. The ear lobe, or other appropriate portion of the patient's body is to be clamped between the pads 68 and 70 and the plate 72.

It is to be noted that the planar surfaces of the pads 68 and 70 which will be in contact with the ear lobe are specially configured into what is termed a waffle pattern. This type of pattern facilitates contact with the acupuncture point.

In a manner that has been described previously, the housing 62 includes a knob 74 which is to not only turn on the electrical pulses, but also to select the type of waveform. Also, knob 76 is to be used to select the desired frequency of the electrical pulses. Knob 78 is to select the intensity for the conductor 54 and knob 80 is to select the intensity for the conductor 56. It is to be noted that the intensity of the electrical pulses supplied to each of the clips 60 can be individually varied, but that the frequency rate for both would be what is selected by knob 76. Also, the waveform would be the same for each of the clips 60. An indicator light 82 is provided on the housing 52 which is to indicate whether the unit is operating and also visually represent the frequency rate similar to light 22.

What is claimed is:

1. An electrical pulse acupressure system adapted to be worn by a human being in contact with the ear, said system comprising:

an electrical pulse generating means, said electrical pulse generating means located within a housing, said housing including special structure means for facilitating connection with the ear;

an electrical pulse applicator, said applicator including means to closely conform in a tight fitting manner with the interior of the ear, said applicator to be carried by the human being, metallic nodule means mounted within an exterior surface of said applicator, said applicator to receive electrical pulses from said electrical pulse generating means and conduct such through said metallic nodule means into the body of the human being, said nodule means adapted to be located against at least one acupuncture point of the body of the human being to thereby treat a corresponding body function said nodule means comprising of plurality of separate nodules; and a polygonal shaped plug having a plurality of electrical connectors, said electrical connectors being electrically connected to said electrical pulse generating means, said applicator having a polygonal shaped recess, said plug matingly fitted within said recess, said electrical connectors electrically connecting with said nodules.

2. The system as defined in claim 1 wherein:
   said electrical pulse generating means to transmit a variety of different pulse waveforms to said metallic nodule means to thereby be capable of selecting different patterns of pulses for different types of treatment.

3. The system as defined in claim 1 wherein:
   said special structure means comprising an arcuate housing to exteriorly conform to the ear and an extension to extend partially into the interior of the ear.

4. The system as defined in claim 3 wherein:
   said electrical pulse generating means to transmit a variety of differnt pulse waveforms to said metallic nodule means to thereby be capable of selecting different patterns of pulses for different types of treatment.

5. The system as defined in claim 1 wherein:
   said special structure means comprising a preformed housing to be located substantially entirely within the ear.

6. The system as defined in claim 5 wherein:
   said electrical pulse generating means to transmit a variety of different pulse waveforms to said metallic nodule means to thereby be capable of selecting different patterns of pulses for different types of treatment.

* * * * *